(12) United States Patent
Yamaguchi et al.

(10) Patent No.: US 10,889,623 B2
(45) Date of Patent: *Jan. 12, 2021

(54) PRODUCTION METHOD FOR RUBBER PARTICLES HAVING MEMBRANE-BINDING PROTEIN BOUND THERETO, PRODUCTION METHOD FOR PNEUMATIC TIRE, AND PRODUCTION METHOD FOR RUBBER PRODUCT

(71) Applicants: SUMITOMO RUBBER INDUSTRIES, LTD., Kobe (JP); TOHOKU UNIVERSITY, Sendai (JP)

(72) Inventors: Haruhiko Yamaguchi, Kobe (JP); Yukino Inoue, Kobe (JP); Kazuhisa Fushihara, Kobe (JP); Seiji Takahashi, Sendai (JP); Satoshi Yamashita, Sendai (JP); Toru Nakayama, Sendai (JP); Yuzuru Tozawa, Saitama (JP)

(73) Assignees: SUMITOMO RUBBER INDUSTRIES, LTD., Kobe (JP); TOHOKU UNIVERSITY, Sendai (JP)

( * ) Notice: Subject to any disclaimer, the term of this patent is extended or adjusted under 35 U.S.C. 154(b) by 371 days.

This patent is subject to a terminal disclaimer.

(21) Appl. No.: 15/579,499

(22) PCT Filed: May 31, 2016

(86) PCT No.: PCT/JP2016/065942
§ 371 (c)(1),
(2) Date: Dec. 4, 2017

(87) PCT Pub. No.: WO2017/002504
PCT Pub. Date: Jan. 5, 2017

(65) Prior Publication Data
US 2018/0355000 A1    Dec. 13, 2018

(30) Foreign Application Priority Data
Jun. 30, 2015 (JP) .................. 2015-131023

(51) Int. Cl.
 *C07K 14/415* (2006.01)
 *B60C 1/00* (2006.01)
 (Continued)

(52) U.S. Cl.
 CPC ............ *C07K 14/415* (2013.01); *B29D 30/00* (2013.01); *B29D 30/0601* (2013.01); *B60C 1/00* (2013.01);
 (Continued)

(58) Field of Classification Search
None
See application file for complete search history.

(56) References Cited

U.S. PATENT DOCUMENTS 10,000,774 B2   6/2018 Yamaguchi
10,385,362 B2   8/2019 Inoue et al.
(Continued)

FOREIGN PATENT DOCUMENTS

CN   104684987 A    6/2015
EP   3 097 775 A1   11/2016
(Continued)

OTHER PUBLICATIONS

Yokoyama, "Development of Membrane Protein-synthesizing System Without Using Cells", NPG Nature Asia-Pacific, vol. 7, No. 4-5, 2010, pp. 28-29, with English translation.
(Continued)

*Primary Examiner* — Kagnew H Gebreyesus
(74) *Attorney, Agent, or Firm* — Birch, Stewart, Kolasch & Birch, LLP

(57) ABSTRACT

The present invention provides a method for producing rubber particles bound to a membrane-associated protein by cell-free protein synthesis. The present invention relates to a method for producing rubber particles bound to a membrane-associated protein, the method including the step of
(Continued)

performing protein synthesis in the presence of both rubber particles and a cell-free protein synthesis solution containing an mRNA coding for a membrane-associated protein to bind the membrane-associated protein to the rubber particles.

10 Claims, 2 Drawing Sheets

Specification includes a Sequence Listing.

(51) Int. Cl.
  C08G 81/02   (2006.01)
  B29D 30/00   (2006.01)
  C12N 15/09   (2006.01)
  B29D 30/06   (2006.01)
  C12N 15/62   (2006.01)
  C08H 1/00    (2006.01)

(52) U.S. Cl.
  CPC ............. *C08G 81/02* (2013.01); *C12N 15/09* (2013.01); *C12N 15/62* (2013.01); *B29D 2030/0055* (2013.01); *C08H 1/00* (2013.01); *C08J 2307/02* (2013.01)

(56) References Cited

U.S. PATENT DOCUMENTS

| | | |
|---|---|---|
| 2015/0266988 A1 | 9/2015 | Kojima et al. |
| 2017/0051313 A1 | 2/2017 | Inoue et al. |
| 2018/0171364 A1 | 6/2018 | Yamaguchi et al. |

FOREIGN PATENT DOCUMENTS

| | | |
|---|---|---|
| JP | 2003-18999 A | 1/2003 |
| JP | 2003-310295 A | 11/2003 |
| JP | 2005-500840 A | 1/2005 |
| JP | 2005-225796 A | 8/2005 |
| JP | 2005-308412 A | 11/2005 |
| JP | 2005-312436 A | 11/2005 |
| JP | 2009-221306 A | 10/2009 |
| JP | 2010-119373 A | 6/2010 |
| JP | 2010-132594 A | 6/2010 |
| JP | 2011-52146 A | 3/2011 |
| JP | 2011-188776 A | 9/2011 |
| JP | 5035871 B2 | 9/2012 |
| JP | 2014-11972 A | 1/2014 |
| JP | 5383197 B2 | 1/2014 |
| JP | 2014-227487 A | 12/2014 |
| JP | 2015-136296 A | 7/2015 |
| JP | 2016-93186 A | 5/2016 |
| JP | 2016-149973 A | 8/2016 |
| JP | 2016-154458 A | 9/2016 |
| WO | WO 03/010294 A2 | 2/2003 |

OTHER PUBLICATIONS

Aoki et al., "Identification of Laticifer-specific Genes and their Promoter Regions from a Natural Rubber Producing Plant *Hevea brasiliensis*," Plant Science, vol. 225, 2014 (Available online May 12, 2014), pp. 1-8.
Berthelot et al., "Hevea brasiliensis REF (Hev b 1) and SRPP (Hev b 3): An Overview on Rubber Particle Proteins," Biochimie, vol. 106, 2014 (Available online Jul. 11, 2014), pp. 1-9.
Branden et al., "Introduction to Protein Structure," Garland Publishing Inc., New York, 1991, p. 247 (3 pages total).
Brasher et al., "A Two-component Enzyme Complex is Required for Dolichol Biosynthesis in Tomato," The Plant Journal, vol. 82, 2015 (published online Apr. 21, 2015), pp. 903-914.
Dai et al., "In-depth proteome analysis of the rubber particle of *Hevea brasiliensis* (para rubber tree)," Plant Molecular Biology, vol. 82, 2013 (published online Apr. 4, 2013), pp. 155-168.

Epping et al., "A rubber transferase activator is necessary for natural rubber biosynthesis in dandelion," Nature Plants, vol. 1, Article No. 15048, May 2015 (published Apr. 27, 2015), XP055372960, 27 pages total.
Goodman, "Polymer biosynthesis: Rubber ramps up," Nature Chemical Biology, vol. 11, No. 7, Jul. 2015, p. 448, XP055373184.
Harrison et al., "Nogo-B receptor is necessary for cellular dolichol biosynthesis and protein N-glycosylation," The EMBO Journal, vol. 30, No. 12, 2011 (published online May 13, 2011), pp. 2490-2500.
Hillebrand et al., "Down-Regulation of Small Rubber Particle Protein Expression Affects Integrity of Rubber Particles and Rubber Content in Taraxacum brevicorniculatum," PLoS ONE, vol. 7, Issue 7, e41874, Jul. 23, 2012, pp. 1-9.
Hoffman et al., "The Who, What, and Where of Plant Polyprenol Biosynthesis Point to Thylakoid Membranes and Photosynthetic Performance," The Plant Cell, vol. 29, Jul. 2017, pp. 1552-1553.
International Preliminary Report on Patentability and Written Opinion of the International Searching Authority for International Application No. PCT/JP2017/041732, dated Jun. 25, 2019.
International Search Report for International Application No. PCT/JP2016/069172, dated Sep. 6, 2016, with English translation.
International Search Report for International Application No. PCT/JP2017/041732, dated Feb. 20, 2018.
Laibach et al., "Identification of a Taraxacum Brevicorniculatum Rubber Elongation Factor Protein that is Localized on Rubber Particles and Promotes Rubber Biosynthesis," The Plant Journal, vol. 82, 2015 (published online Mar. 24, 2015), pp. 609-620.
Madin et al., "A Highly Efficient and Robust Cell-free Protein Synthesis System Prepared from Wheat Embryos: Plants Apparently Contain a Suicide System Directed at Ribosomes," Proceedings of the National Academy of Sciences USA, vol. 97, No. 2, Jan. 18, 2000, pp. 559-564 (7 pages total).
Nguyen et al., "cis-Prenyltransferase Interacts with a Nogo-B Receptor Homolog for Dolichol Biosynthesis in Panax ginseng Meyer," Journal of Ginseng Research, vol. 41, 2017 (Available online Jan. 27, 2017), pp. 403-410.
Ohya et al., "Biosynthesis of Natural Rubber and Other Natural Polyisoprenoids," Biopolymers Online, Published online Jan. 15, 2005, 43 pages.
Park et al., "Mutation of Nogo-B receptor, a subunit of cis-prenyltransferase, causes a congenital disorder of glycosylation," Cell Metabolism, vol. 20, Sep. 2, 2014 (published Jul. 24, 2014), pp. 448-457.
Phatthiya et al., "Cloning and Expression of the Gene Encoding Solanesyl Diphosphate Synthase from Hevea Brasiliensis", Plant Science, vol. 172, 2007, pp. 824-831.
Post et al., "Laticifer-Specific cis-Prenyltransferase Silencing Affects the Rubber, Triterpene, and Inulin Content of Taraxacum brevicorniculatum," Plant Physiology, Mar. 2012, vol. 158, pp. 1406-1417.
Priya et al., "Differential expression pattern of rubber elongation factor (REF) mRNA transcripts from high and low yielding clones of rubber tree (*Hevea brasiliensis* Muell. Arg.)," Plant Cell Reports, vol. 26, 2007 (Published online Jul. 14, 2007), pp. 1833-1838.
Priya et al., "Molecular Cloning and Characterization of the Rubber Elongation Factor Gene and its Promoter Sequence from Rubber Tree (*Hevea brasiliensis*): A Gene Involved in Rubber Biosynthesis," Plant Science, vol. 171, 2006 (published online Jun. 13, 2006), pp. 470-480.
Qu et al., "A lettuce (*Lactuca sativa*) homolog of human Nogo-B receptor interacts with cis-prenyltransferase and is necessary for natural rubber biosynthesis," J. Biol. Chem., vol. 290, No. 4, Jan. 23, 2015, pp. 1898-1914, abstract provided only.
Rahman et al., "Draft genome sequence of the rubber tree *Hevea brasiliensis*," BMC Genomics, vol. 14, No. 75, 2013, pp. 1-15.
Rahman et al., "TSA: Hevea brasiliensis contig33814, mRNA sequence," Database GenBank [online], Accession No. JT945746, Feb. 5, 2013, pp. 1-2.
Rojruthai et al., "In Vitro Synthesis of High Molecular Weight Rubber by Hevea Small Rubber Particles," Journal of Bioscience and Bioengineering, vol. 109, No. 2, 2010 (Available online Sep. 18, 2009), pp. 107-114.

(56) References Cited

OTHER PUBLICATIONS

Surmacz et al., "cis-Prenyltransferase AtCPT6 produces a family of very short-chain polyisoprenoids in planta," Biochimica et Biophysica Acta, vol. 1841, 2014 (available online Dec. 1, 2013), pp. 240-250.
Takahashi et al., "Characterization of cis-prenyltransferases from the rubber producing plant *Hevea brasiliensis* heterologously expressed in yeast and plant cells," Plant Biotechnology, vol. 29, Oct. 20, 2012 (published online Aug. 30, 2012), pp. 411-417 (8 pages total).
Takahashi et al., "Molecular Insights of Natural Rubber Biosynthesis—An Approach from Prenyltransferase Gene Analysis", The Society of Rubber Science and Techneiogy, vol. 76, No. 12, 2003, pp. 446-452, with 1 page abstract.
Tata et al., "Lacticifer Tissue-Specific Activation of the Hevea SRPP Promoter in Taraxacum brevicorniculatum and its Regulation by Light, Tapping and Cold Stress," Industrial Crops and Products, vol. 40, 2012, pp. 219-224.
Unknown, "Successful in Vitro Synthesis of Natural Rubber by Bioengineering—Contributing to the Stable Supply of Natural Rubber with New Molecular Structure", Tohoku University, Nov. 16, 2016, 4 pages total.
Xiang et al., "Proteome Analysis of the Large and the Small Rubber Particles of Hevea brasiliensis Using 2D-DIGE," Plant Physiology and Biochemistry, vol. 60, 2012 (Available online Sep. 5, 2012), pp. 207-213.
Yamashita et al., "Identification and Reconstitution of the Rubber Biosynthetic Machinery on Rubber Particles from Hevea Brasiliensis", eLife, vol. 5, No. 19022, Oct. 28, 2016, pp. 1-28.
Asawatreratanakul et al., "Molecular Cloning, Expression and Characterization of cDNA Encoding cis-prenyltransferases from Hevea brasiliensis," Eur. J. Biochem., vol. 270, 2003, pp. 4671-4680.
International Search Report for International Application No. PCT/JP2016/065942, dated Jun. 28, 2016.

M : Marker
1,4,7,10 : Before separation of protein synthesis solution
2,5,8,11 : Separated supernatant
3,6,9,12 : Reacted rubber particles M : Marker
1 : Before separation of protein synthesis solution
2 : Separated supernatant
3 : Reacted rubber particles

SEQUENCE LISTING

```
<160> NUMBER OF SEQ ID NOS: 12

<210> SEQ ID NO 1
<211> LENGTH: 34
<212> TYPE: DNA
<213> ORGANISM: Artificial Sequence
<220> FEATURE:
<223> OTHER INFORMATION: PRIMER-1

<400> SEQUENCE: 1
tttggatccg atggaattat acaacggtga gagg                                34

<210> SEQ ID NO 2
<211> LENGTH: 39
<212> TYPE: DNA
<213> ORGANISM: Artificial Sequence
<220> FEATURE:
<223> OTHER INFORMATION: PRIMER-2

<400> SEQUENCE: 2
tttgcggccg cttattttaa gtattcctta tgtttctcc                           39

<210> SEQ ID NO 3
<211> LENGTH: 873
<212> TYPE: DNA
<213> ORGANISM: Hevea brasiliensis

<400> SEQUENCE: 3
atggaattat acaacggtga gaggccaagt gtgttcagac ttttagggaa gtatatgaga     60
aaagggttat atagcatcct aacccagggt cccatcccta ctcatattgc cttcatattg    120
gatggaaaca ggaggtttgc taagaagcat aaactgccag aaggaggtgg tcataaggct    180
ggatttttag ctcttctgaa cgtactaact tattgctatg agttaggagt gaaatatgcg    240
actatctatg cctttagcat cgataatttt cgaaggaaac ctcatgaggt tcagtacgta    300
atggatctaa tgctggagaa gattgaaggg atgatcatgg aagaaagtat catcaatgca    360
tatgatattt gcgtacgttt tgtgggtaac ctgaagcttt taagtgagcc agtcaagacc    420
gcagcagata agattatgag ggctactgcc aacaattcca aatgtgtgct tctcattgct    480
gtatgctata cttcaactga tgagatcgtg catgctgttg aagaatcctc tgaattgaac    540
tccaatgaag tttgtaacaa tcaagaattg gaggaggcaa atgcaactgg aagcggtact    600
gtgattcaaa ttgagaacat ggagtcgtat tctggaataa aacttgtaga ccttgagaaa    660
aacacctaca taaatcctta tcctgatgtt ctgattcgaa cttctgggga gacccgtctg    720
agcaactact tactttggca gactactaat tgcatactgt attctcctca tgcactgtgg    780
ccagagattg gtcttcgaca cgtggtgtgg gcagtaatta acttccaacg tcattattct    840
tacttggaga aacataagga atacttaaaa taa                                 873

<210> SEQ ID NO 4
<211> LENGTH: 290
<212> TYPE: PRT
<213> ORGANISM: Hevea brasiliensis

<400> SEQUENCE: 4
```

```
Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile
            20                  25                  30

Pro Thr His Ile Ala Phe Ile Leu Asp Gly Asn Arg Arg Phe Ala Lys
        35                  40                  45

Lys His Lys Leu Pro Glu Gly Gly His Lys Ala Gly Phe Leu Ala
    50                  55                  60

Leu Leu Asn Val Leu Thr Tyr Cys Tyr Glu Leu Gly Val Lys Tyr Ala
65                  70                  75                  80

Thr Ile Tyr Ala Phe Ser Ile Asp Asn Phe Arg Arg Lys Pro His Glu
                85                  90                  95

Val Gln Tyr Val Met Asp Leu Met Leu Glu Lys Ile Glu Gly Met Ile
            100                 105                 110

Met Glu Glu Ser Ile Ile Asn Ala Tyr Asp Ile Cys Val Arg Phe Val
            115                 120                 125

Gly Asn Leu Lys Leu Leu Ser Glu Pro Val Lys Thr Ala Ala Asp Lys
    130                 135                 140

Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
            180                 185                 190

Ala Asn Ala Thr Gly Ser Gly Thr Val Ile Gln Ile Glu Asn Met Glu
    195                 200                 205

Ser Tyr Ser Gly Ile Lys Leu Val Asp Leu Glu Lys Asn Thr Tyr Ile
210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

His Ala Leu Trp Pro Glu Ile Gly Leu Arg His Val Val Trp Ala Val
            260                 265                 270

Ile Asn Cys Gln Arg His Tyr Ser Tyr Leu Glu Lys His Lys Glu Tyr
    275                 280                 285

Leu Lys
    290

<210> SEQ ID NO 5
<211> LENGTH: 31
<212> TYPE: DNA
<213> ORGANISM: Artificial Sequence
<220> FEATURE:
<223> OTHER INFORMATION: PRIMER-3

<400> SEQUENCE: 5
tttctcgaga tggatttgaa acctggagct g                                    31

<210> SEQ ID NO 6
<211> LENGTH: 33
<212> TYPE: DNA
<213> ORGANISM: Artificial Sequence
<220> FEATURE:
<223> OTHER INFORMATION: PRIMER-4

<400> SEQUENCE: 6
```

```
tttctcgagt catgtaccat aattttgctg cac                                      33
```

<210> SEQ ID NO 7
<211> LENGTH: 774
<212> TYPE: DNA
<213> ORGANISM: Hevea brasiliensis

<400> SEQUENCE: 7

```
atggatttga aacctggagc tggagggcag agagttaatc gattagtgga tccgattagt    60
tatcattttc ttcaatttct gtggcgtact ctacatcttc ttgtcagctt atggtacctt   120
caagttagta tggtccaaat gatcgaaggc tttctaatct ctagtggact tgtgaaacgc   180
tatggagccc tcgatattga aaggtccgg taccttgcca ttgtggtaga tagtgaagaa    240
gcttaccaaa tttctaaagt tattcagctt ttgaaatggg tggaagatat gggtgtgaaa   300
catttatgcc tctatgattc aaaaggagtt ctcaagacaa acaagaaaac catcatggag   360
agtttgaaca atgctatgcc atttgaggaa gcagttgaaa aagatgtttt actggaccag   420
aaacagatga ctgtggaatt tgcttccagc tccgatggaa aggaagcaat aaccagggca   480
gctaacgtac tctttatgaa gtatttgaag tatgctaaaa ctggtgtagg aaaggaagaa   540
ccatgcttta cagaagatca aatggatgag gcactaaaag ctataggtta caagggccg    600
gaacctgact tgctattaat ttatggaccct gttagatgcc atctaggttt ctcaccgtgg   660
agacttcgat atactgagat ggtgcatatg ggacccttga ggtacatgaa cctcggttca   720
ctaaaaaagg ccattcacag gttcacaaca gtgcagcaaa attatggtac atga          774
```

<210> SEQ ID NO 8
<211> LENGTH: 257
<212> TYPE: PRT
<213> ORGANISM: Hevea brasiliensis

<400> SEQUENCE: 8

```
Met Asp Leu Lys Pro Gly Ala Gly Gly Gln Arg Val Asn Arg Leu Val
1               5                   10                  15

Asp Pro Ile Ser Tyr His Phe Leu Gln Phe Leu Trp Arg Thr Leu His
            20                  25                  30

Leu Leu Val Ser Leu Trp Tyr Leu Gln Val Ser Met Val Gln Met Ile
        35                  40                  45

Glu Gly Phe Leu Ile Ser Ser Gly Leu Val Lys Arg Tyr Gly Ala Leu
    50                  55                  60

Asp Ile Asp Lys Val Arg Tyr Leu Ala Ile Val Val Asp Ser Glu Glu
65                  70                  75                  80

Ala Tyr Gln Ile Ser Lys Val Ile Gln Leu Leu Lys Trp Val Glu Asp
                85                  90                  95

Met Gly Val Lys His Leu Cys Leu Tyr Asp Ser Lys Gly Val Leu Lys
            100                 105                 110

Thr Asn Lys Lys Thr Ile Met Glu Ser Leu Asn Asn Ala Met Pro Phe
        115                 120                 125

Glu Glu Ala Val Glu Lys Asp Val Leu Leu Asp Gln Lys Gln Met Thr
    130                 135                 140

Val Glu Phe Ala Ser Ser Ser Asp Gly Lys Glu Ala Ile Thr Arg Ala
145                 150                 155                 160

Ala Asn Val Leu Phe Met Lys Tyr Leu Lys Tyr Ala Lys Thr Gly Val
                165                 170                 175

Gly Lys Glu Glu Pro Cys Phe Thr Glu Asp Gln Met Asp Glu Ala Leu
```

```
              180                 185                 190
Lys Ala Ile Gly Tyr Lys Gly Pro Glu Pro Asp Leu Leu Leu Ile Tyr
            195                 200                 205
Gly Pro Val Arg Cys His Leu Gly Phe Ser Pro Trp Arg Leu Arg Tyr
            210                 215                 220
Thr Glu Met Val His Met Gly Pro Leu Arg Tyr Met Asn Leu Gly Ser
225                 230                 235                 240
Leu Lys Lys Ala Ile His Arg Phe Thr Thr Val Gln Gln Asn Tyr Gly
            245                 250                 255
Thr

<210> SEQ ID NO 9
<211> LENGTH: 27
<212> TYPE: DNA
<213> ORGANISM: Artificial Sequence
<220> FEATURE:
<223> OTHER INFORMATION: PRIMER-5

<400> SEQUENCE: 9
ggatccgatg ttgtctattc tctcttc                                      27

<210> SEQ ID NO 10
<211> LENGTH: 27
<212> TYPE: DNA
<213> ORGANISM: Artificial Sequence
<220> FEATURE:
<223> OTHER INFORMATION: PRIMER-6

<400> SEQUENCE: 10
actagttcaa acccgacagc caaatcg                                      27

<210> SEQ ID NO 11
<211> LENGTH: 909
<212> TYPE: DNA
<213> ORGANISM: Arabidopsis thaliana

<400> SEQUENCE: 11
atgttgtcta ttctctcttc tcttttatct ctccttttc tgtttatcat ctcttgtttc    60
ttcatcacaa gccattttg gttccctctt tccttgccaa aaatactcgg attcatcaaa   120
atcacatctt cgagagacga ttatgacaac gagcaacgtg acgagggaac ttatgtggta   180
ggagtggagg agctacaaag agagctgatg ccaagacatg tggcagtgat aatggacgga   240
aaccggagat gggccaaacg ggccggattg ctgacgtcac aaggccacga ggccggagct   300
aaacggctta tagagttctc cgagctttgc tttaaattgg ggattcatac agtttcagct   360
tttgccttct ccacagagaa ttggggaaga cacaagattg aggttaagtg cttgatgtct   420
tgatccaac attcctcaa gtccaagatc caatatttcc aaagagagga aactcgagtt   480
tctgttatcg gaaccctaac gaagatccct gagtctctcc tccgaacagt ccaagagata   540
gaggaagcta cgagaagcta taagaagaag catctcatat tggcaataga ttacagcggg   600
agattagaca tcttgcgagc ttgcaagagt attgtgaaga aatcagaaaa agggttgatc   660
cgagaggaag atgtagacga ggcattgatc gaaagagagc ttctgacaaa ttgtactgag   720
ttcccaagtc ctgatctatt gattaggaca agtggagaac agaggattag taacttcttc   780
ttgtggcaac ttgcttatac agagctcttc ttctcgccgg tcctttggcc tgatttcgat   840
aaggataagc ttctagaggc cctggtttcg tatcagcgcc gggaaagacg atttggctgt   900
cgggtttga                                                          909
```

```
<210> SEQ ID NO 12
<211> LENGTH: 302
<212> TYPE: PRT
<213> ORGANISM: Arabidopsis thaliana

<400> SEQUENCE: 12

Met Leu Ser Ile Leu Ser Ser Leu Leu Ser Leu Leu Phe Leu Phe Ile
1               5                   10                  15

Ile Ser Cys Phe Phe Ile Thr Ser His Phe Trp Phe Pro Leu Ser Leu
            20                  25                  30

Pro Lys Ile Leu Gly Phe Ile Lys Ile Thr Ser Ser Arg Asp Asp Tyr
        35                  40                  45

Asp Asn Glu Gln Arg Asp Glu Gly Thr Tyr Val Val Gly Val Glu Glu
    50                  55                  60

Leu Gln Arg Glu Leu Met Pro Arg His Val Ala Val Ile Met Asp Gly
65                  70                  75                  80

Asn Arg Arg Trp Ala Lys Arg Ala Gly Leu Leu Thr Ser Gln Gly His
                85                  90                  95

Glu Ala Gly Ala Lys Arg Leu Ile Glu Phe Ser Glu Leu Cys Phe Lys
            100                 105                 110

Leu Gly Ile His Thr Val Ser Ala Phe Ala Phe Ser Thr Glu Asn Trp
        115                 120                 125

Gly Arg His Lys Ile Glu Val Lys Cys Leu Met Ser Leu Ile Gln His
    130                 135                 140

Tyr Leu Lys Ser Lys Ile Gln Tyr Phe Gln Arg Glu Glu Thr Arg Val
145                 150                 155                 160

Ser Val Ile Gly Asn Leu Thr Lys Ile Pro Glu Ser Leu Leu Arg Thr
                165                 170                 175

Val Gln Glu Ile Glu Glu Ala Thr Arg Ser Tyr Lys Lys Lys His Leu
            180                 185                 190

Ile Leu Ala Ile Asp Tyr Ser Gly Arg Leu Asp Ile Leu Arg Ala Cys
        195                 200                 205

Lys Ser Ile Val Lys Lys Ser Glu Lys Gly Leu Ile Arg Glu Glu Asp
    210                 215                 220

Val Asp Glu Ala Leu Ile Glu Arg Glu Leu Leu Thr Asn Cys Thr Glu
225                 230                 235                 240

Phe Pro Ser Pro Asp Leu Leu Ile Arg Thr Ser Gly Glu Gln Arg Ile
                245                 250                 255

Ser Asn Phe Phe Leu Trp Gln Leu Ala Tyr Thr Glu Leu Phe Phe Ser
            260                 265                 270

Pro Val Leu Trp Pro Asp Phe Asp Lys Asp Lys Leu Leu Glu Ala Leu
        275                 280                 285

Val Ser Tyr Gln Arg Arg Glu Arg Arg Phe Gly Cys Arg Val
    290                 295                 300
```

PRODUCTION METHOD FOR RUBBER PARTICLES HAVING MEMBRANE-BINDING PROTEIN BOUND THERETO, PRODUCTION METHOD FOR PNEUMATIC TIRE, AND PRODUCTION METHOD FOR RUBBER PRODUCT

PARTIES TO A JOINT RESEARCH AGREEMENT

Sumitomo Rubber Industries, LTD., Tohoku University, and Kanazawa University are parties to a "joint research agreement" as defined in 35 U.S.C. 103(c)(3).

TECHNICAL FIELD

The present invention relates to a method for producing rubber particles bound to a membrane-associated protein, a method for producing a pneumatic tire, and a method for producing a rubber product.

BACKGROUND ART

The conventional methods for preparing membrane-associated proteins require culturing large quantities of cells (e.g. *Escherichia coli*, yeasts) overexpressing membrane-associated proteins, extracting the membrane-associated proteins with surfactants, and purifying the extracted proteins. However, the optimal surfactant for extracting a membrane-associated protein is different from protein to protein, and the choice of a suitable surfactant is important in the preparation of membrane-associated proteins.

Because of their hydrophobic nature, membrane-associated proteins are difficult even to purify. Further, once they are solubilized with surfactants, their structure change, and thus the proteins, when bound again to the membranes, do not always retain their original structure.

In order to reveal the true function and activity of membrane-associated proteins, it is necessary to evaluate the function of the proteins with their proper structure when they are bound to membranes. However, such evaluation has been considered technically difficult for the above reason.

Recently, attempts have been made to synthesize and collect membrane proteins retaining their biological functions (i.e. in native state) by producing membrane-associated proteins by cell-free protein synthesis, instead of producing membrane-associated proteins in cultured cells, and allowing the proteins to stand with liposomes (artificial membranes) in place of cell membranes (see, for example, Patent Literature 1). Also disclosed are: methods in which a membrane-associated protein is synthesized by cell-free protein synthesis, and the produced membrane-associated protein is immobilized by embedding it into a lipid bilayer fixed on a substrate; and high yield synthesis of membrane-associated proteins achieved by cell-free protein synthesis in the presence of membrane vesicles (see, for example, Patent Literatures 2 and 3).

CITATION LIST

Patent Literature

Patent Literature 1: JP 2005-225796 A
Patent Literature 2: JP 2010-132594 A
Patent Literature 3: JP 5383197 B

SUMMARY OF INVENTION

Technical Problem

As described above, the cell-free protein synthesis of membrane-associated proteins in the presence of liposomes, lipid bilayers, or membrane vesicles has been studied. Liposomes are artificially produced as lipid bilayer membranes formed of phospholipids, glyceroglycolipids, cholesterol, or other components. Thus, no protein is bound to the surface of the produced liposomes.

In contrast, although rubber particles collected from the latex of rubber-producing plants are also coated with a lipid membrane, the membrane of the rubber particles is a naturally derived membrane in which proteins that have been synthesized in the plants are already bound to the surface of the membrane. The lipid membrane of rubber particles is generally considered to be a monolayer.

Under the above-described circumstances, there has not yet been any attempt to perform cell-free protein synthesis of membrane-associated proteins in the presence of rubber particles.

The present invention aims to solve the above problems and provide a method for producing rubber particles bound to a membrane-associated protein by cell-free protein synthesis.

Solution to Problem

The present invention relates to a method for producing rubber particles bound to a membrane-associated protein, the method including the step of performing protein synthesis in the presence of both rubber particles and a cell-free protein synthesis solution containing an mRNA coding for a membrane-associated protein to bind the membrane-associated protein to the rubber particles.

Preferably, the cell-free protein synthesis solution contains a germ extract.

Preferably, the germ extract is derived from wheat.

Preferably, the rubber particles are present in the cell-free protein synthesis solution at a concentration of 5 to 50 g/L.

Preferably, the rubber particles are washed with a surfactant before being combined with the cell-free protein synthesis solution.

Preferably, the surfactant is an amphoteric surfactant, and the rubber particles are washed with the surfactant at a concentration within three times a critical micelle concentration of the surfactant.

Preferably, the surfactant is CHAPS.

Preferably, the protein synthesis is carried out by a dialysis method.

Preferably, the mRNA coding for a membrane-associated protein is additionally added during the protein synthesis reaction.

The present invention also relates to a method for producing a pneumatic tire, the method including the steps of: synthesizing rubber from rubber particles produced by the method for producing rubber particles; kneading the rubber with an additive to obtain a kneaded mixture; building a green tire from the kneaded mixture; and vulcanizing the green tire.

The present invention also relates to a method for producing a rubber product, the method including the steps of: synthesizing rubber from rubber particles produced by the method for producing rubber particles; kneading the rubber with an additive to obtain a kneaded mixture; forming a raw rubber product from the kneaded mixture; and vulcanizing the raw rubber product.

Advantageous Effects of Invention

The method for producing rubber particles bound to a membrane-associated protein of the present invention includes the step of performing protein synthesis in the presence of both rubber particles and a cell-free protein synthesis solution containing an mRNA coding for a membrane-associated protein to bind the membrane-associated protein to the rubber particles. It is thus possible to produce rubber particles bound to a membrane-associated protein by cell-free protein synthesis, and to bind a membrane-associated protein to rubber particles while maintaining its original structure to modify the properties of the rubber particles.

The method for producing a pneumatic tire of the present invention includes the steps of: synthesizing rubber from rubber particles produced by the method for producing rubber particles of the present invention; kneading the rubber with an additive to obtain a kneaded mixture; building a green tire from the kneaded mixture; and vulcanizing the green tire. With this method, pneumatic tires are produced from rubber produced from rubber particles produced by a method that can modify the properties of rubber particles during the rubber particle production. Thus, it is possible to use plant resources effectively to produce environmentally friendly pneumatic tires.

The method for producing a rubber product of the present invention includes the steps of: synthesizing rubber from rubber particles produced by the method for producing rubber particles of the present invention; kneading the rubber with an additive to obtain a kneaded mixture; forming a raw rubber product from the kneaded mixture; and vulcanizing the raw rubber product. With this method, rubber products are produced from rubber produced from rubber particles produced by a method that can modify the properties of rubber particles during the rubber particle production. Thus, it is possible to use plant resources effectively to produce environmentally friendly rubber products.

DESCRIPTION OF EMBODIMENTS

Figure 1:
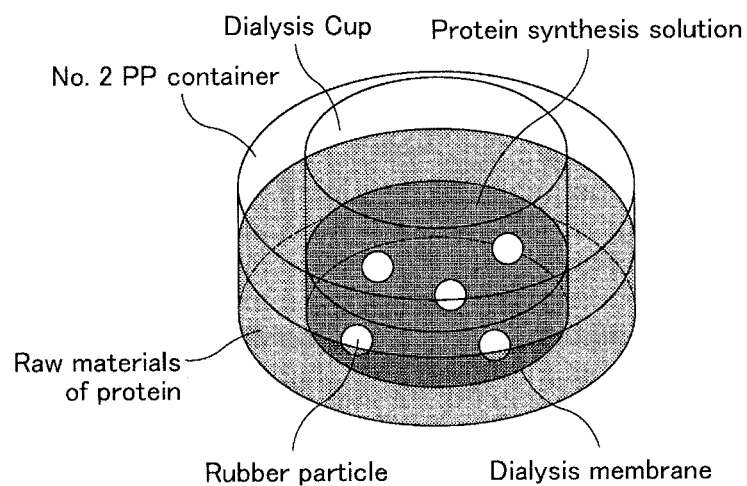
FIG. 1 is an outline diagram illustrating a dialysis process in Examples.

The method for producing rubber particles bound to a membrane-associated protein of the present invention includes the step of performing protein synthesis in the presence of both rubber particles and a cell-free protein synthesis solution containing an mRNA coding for a membrane-associated protein to bind the membrane-associated protein to the rubber particles. In other words, a membrane-associated protein can be bound to rubber particles by performing protein synthesis in the presence of both the rubber particles and a cell-free protein synthesis solution containing an mRNA coding for the membrane-associated protein, or more specifically, using a mixture of the rubber particles with a cell-free protein synthesis solution containing an mRNA coding for the membrane-associated protein.

As described earlier, since liposomes are artificially produced as lipid bilayer membranes formed of phospholipids, glyceroglycolipids, cholesterol, or other components, no protein is bound to the surface of the produced liposomes. In contrast, although rubber particles collected from the latex of rubber-producing plants are also coated with a lipid membrane, the membrane of the rubber particles is a naturally derived membrane in which proteins that have been synthesized in the plants are already bound to the surface of the membrane. Hence, binding of an additional protein to rubber particles that are already bound to and coated with proteins is expected to be more difficult than binding to liposomes not bound to any protein. There is also concern that the proteins already bound to rubber particles could inhibit cell-free protein synthesis.

For these reasons, difficulties have been anticipated in performing cell-free protein synthesis in the presence of rubber particles. Under such circumstances, the present inventors have made studies to perform cell-free protein synthesis of a membrane-associated protein in the presence of rubber particles, which had never been attempted in the past, and they have first discovered that rubber particles bound to a membrane-associated protein can be produced by performing cell-free protein synthesis in the presence of rubber particles. With this method, it is possible to bind a membrane-associated protein to rubber particles while maintaining its original structure to modify the properties of the rubber particles.

The production method of the present invention may include any other step as long as it involves the above step, and each step may be performed once or repeated multiple times.

In the present invention, the amount of the membrane-associated protein to be bound to the rubber particles is not particularly limited.

Herein, binding of a membrane-associated protein to rubber particles by protein synthesis in the presence of both the cell-free protein synthesis solution and the rubber particles means that, for example, the membrane-associated protein synthesized by the protein synthesis is fully or partially incorporated into the rubber particles or inserted into the membrane structure of the rubber particles. It is not limited to these embodiments and also includes embodiments in which, for example, the protein is localized on the surface or inside of the rubber particles. Moreover, the concept of the membrane-associated protein bound to rubber particles also includes embodiments in which the protein forms a complex with another membrane-associated protein bound to the rubber particles as described above so as to be present in the form of the complex on the rubber particles.

The origin of the rubber particles is not particularly limited. For example, the rubber particles may be derived from the latex of a rubber-producing plant such as *Hevea brasiliensis, Taraxacum kok-saghyz, Parthenium argentatum, Sonchus oleraceus*, or *Ficus elastica*.

The particle size of the rubber particles is also not particularly limited. Rubber particles having a predetermined particle size may be sorted out and used, or a mixture of rubber particles having different particle sizes may be used. When rubber particles having a predetermined particle size are sorted out and used, the rubber particles may be either small rubber particles (SRP) having a small particle size or large rubber particles (LRP) having a large particle size.

Commonly used methods may be employed for sorting out the rubber particles having a predetermined particle size, including, for example, methods involving centrifugation, preferably multistage centrifugation. A specific method includes centrifugation at 500-1,500×g, centrifugation at 1,700-2,500×g, centrifugation at 7,000-9,000×g, centrifugation at 15,000-25,000×g, and centrifugation at 40,000-60,000×g, carried out in that order. The duration of each centrifugation treatment is preferably at least 20 minutes, more preferably at least 30 minutes, still more preferably at least 40 minutes, but preferably 120 minutes or less, more preferably 90 minutes or less. The temperature for each centrifugation treatment is preferably 0° C. to 10° C., more preferably 2° C. to 8° C., particularly preferably 4° C.

The mRNA coding for a membrane-associated protein serves as a translation template that can be translated to synthesize the membrane-associated protein. In the production method of the present invention, it may be an mRNA coding for a single membrane-associated protein, or a mixture of two or more mRNAs coding for membrane-associated proteins. In other words, in the present invention, one or two or more membrane-associated proteins may be bound to rubber particles.

The method for preparing the mRNA coding for a membrane-associated protein is not particularly limited as long as the prepared mRNA serves as a translation template that can be translated to synthesize the membrane-associated protein. For example, the mRNA may be prepared by extracting total RNA from for example a tissue of an organism, e.g. by the hot phenol method, synthesizing cDNA from the total RNA, obtaining a DNA fragment of a gene coding for a membrane-associated protein of interest using primers prepared based on the nucleotide sequence data of the gene coding for a membrane-associated protein of interest, and performing an ordinary in vitro transcription reaction of the DNA fragment.

The origin of the mRNA coding for a membrane-associated protein is not particularly limited, but is preferably plants, more preferably at least one selected from the group consisting of plants of the genera *Hevea*, *Sonchus*, *Taraxacum*, and *Parthenium*. Among these, the mRNA is still more preferably derived from at least one species of plant selected from the group consisting of *Hevea brasiliensis*, *Sonchus oleraceus*, *Parthenium argentatum*, and *Taraxacum kok-saghyz*, particularly preferably *Hevea brasiliensis*.

The plant is not particularly limited, and examples include *Hevea* species such as *Hevea brasiliensis*; *Sonchus* species such as *Sonchus oleraceus*, *Sonchus asper*, and *Sonchus brachyotus*; *Solidago* species such as *Solidago altissima*, *Solidago virgaurea* subsp. *asiatica*, *Solidago virgaurea* subsp. *leipcarpa*, *Solidago virgaurea* subsp. *leipcarpa* f. *paludosa*, *Solidago virgaurea* subsp. *gigantea*, and *Solidago gigantea* Ait. var. *leiophylla* Fernald; *Helianthus* species such as *Helianthus annus*, *Helianthus argophyllus*, *Helianthus atrorubens*, *Helianthus debilis*, *Helianthus decapetalus*, and *Helianthus giganteus*; *Taraxacum* species such as dandelion (*Taraxacum*), *Taraxacum venustum* H. Koidz, *Taraxacum hondoense* Nakai, *Taraxacum platycarpum* Dahlst, *Taraxacum japonicum*, *Taraxacum officinale* Weber, *Taraxacum kok-saghyz*, and *Taraxacum brevicorniculatum*; *Ficus* species such as *Ficus carica*, *Ficus elastica*, *Ficus pumila* L., *Ficus erecta* Thumb., *Ficus ampelas* Burm. f., *Ficus benguetensis* Merr., *Ficus irisana* Elm., *Ficus microcarpa* L. f., *Ficus septica* Burm. f., and *Ficus benghalensis*; *Parthenium* species such as *Parthenium argentatum*, *Parthenium hysterophorus*, and *Ambrosia artemisiifolia* (*Parthenium hysterophorus*); lettuce (*Lactuca sativa*); *Ficus benghalensis*; and *Arabidopsis thaliana*.

The membrane-associated protein may be any protein that inherently has properties of binding to membranes in organisms. It may be a protein that inherently exists on rubber particles in rubber-producing plants or a protein that does not exist on rubber particles in nature, preferably a protein that inherently exists on rubber particles in rubber-producing plants. The mode of binding of the membrane-associated protein to membranes is not particularly limited. It may be a membrane-associated protein bound to a large part of the membrane surface, or a membrane-associated protein inserted into and bound to a membrane, or a protein that forms a complex with the membrane-associated protein so as to be present on the membrane surface.

Examples of the membrane-associated protein that inherently exists on rubber particles in rubber-producing plants include cis-prenyltransferase (CPT), Nogo-B receptor (NgBR), rubber elongation factor (REF), small rubber particle protein (SRPP), β-1,3-glucanase, and Hevein.

Such membrane-associated proteins are roughly classified into integral membrane-associated proteins, which have one or more domains embedded in lipid membranes, and peripheral membrane-associated proteins, which are bound only to the surface of lipid membranes, depending on the binding mode. Most integral membrane-associated proteins have one or more transmembrane domains penetrating through the lipid membrane.

Examples of the integral membrane-associated proteins include proteins serving as receptors such as G protein-coupled receptors and proteins serving as channels such as ion channels. Specific examples include cytochrome b561 and muscarinic acetylcholine receptors (multiple pass transmembrane proteins), and P450-reductase (N-terminal single pass transmembrane protein).

Also, specific examples of the peripheral membrane-associated proteins include cytochrome b5 (C-terminal anchored protein).

The membrane-associated protein is preferably a protein that inherently exists on rubber particles in rubber-producing plants and is involved in rubber synthesis, among other proteins. By binding such a protein involved in rubber synthesis to rubber particles, it is possible to increase the rubber synthesis activity of the rubber particles, thereby allowing for more efficient rubber production in reaction vessels (e.g. test tubes, industrial plants).

Specifically, the membrane-associated protein is more preferably at least one selected from the group consisting of CPT, NgBR, REF, and SRPP, still more preferably at least one selected from the group consisting of CPT, NgBR, and REF, particularly preferably CPT and/or NgBR.

In the present invention, cell-free protein synthesis of a membrane-associated protein is performed in the presence of rubber particles. This cell-free protein synthesis may be carried out using the cell-free protein synthesis solution of the present invention in a similar manner to the prior art. The cell-free protein synthesis system used may be a common cell-free protein synthesis means, such as rapid translation system RTS500 (Roche Diagnostics); or wheat germ extracts prepared in accordance with Proc. Natl. Acad. Sci. USA, 97:559-564 (2000), JP-A2000-236896, JP-A2002-125693, and JP-A 2002-204689, or cell-free protein synthesis systems using the wheat germ extracts (JP-A 2002-204689, Proc. Natl. Acad. Sci. USA, 99:14652-14657 (2002)). Systems using germ extracts are preferred among these. Thus, in another suitable embodiment of the present invention, the cell-free protein synthesis solution contains a germ extract.

The source of the germ extract is not particularly limited. From the standpoint of translation efficiency, it is preferred to use a plant-derived germ extract when a plant membrane-associated protein is synthesized by cell-free protein synthesis. It is particularly preferred to use a wheat-derived germ extract. Thus, in another suitable embodiment of the present invention, the germ extract is derived from wheat.

The method for preparing the germ extract is not particularly limited, and may be carried out conventionally, as described in, for example, JP-A 2005-218357.

The cell-free protein synthesis solution used in the present invention preferably further contains a cyclic nucleoside monophosphate derivative or a salt thereof (hereinafter, also referred to simply as "activity enhancer"). Protein synthesis activity can be further increased by the inclusion of the activity enhancer.

The cyclic nucleoside monophosphate derivative or salt thereof is not particularly limited as long as it can increase cell-free protein synthesis activity. Examples include adenosine-3',5'-cyclic monophosphoric acid and its salts; adenosine-3',5'-cyclic monophosphorothioic acid (Sp-isomer) and its salts; adenosine-3',5'-cyclic monophosphorothioic acid (Rp-isomer) and its salts; guanosine-3',5'-cyclic monophosphoric acid and its salts; guanosine-3',5'-cyclic monophosphorothioic acid (Sp-isomer) and its salts; guanosine-3',5'-cyclic monophosphorothioic acid (Rp-isomer) and its salts; 8-bromoadenosine-3',5'-cyclic monophosphoric acid (bromo-cAMP) and its salts; 8-(4-chlorophenylthio)adenosine-3',5'-cyclic monophosphoric acid (chlorophenylthio-cAMP) and its salts; 5,6-dichloro-1-β-D-ribofuranosylbenzimidazole adenosine-3',5'-cyclic monophosphoric acid (dichlororibofuranosylbenzimidazole cAMP) and its salts; adenosine-2',5'-cyclic monophosphoric acid and its salts; adenosine-2',5'-cyclic monophosphorothioic acid (Sp-isomer) and its salts; adenosine-2',5'-cyclic monophosphorothioic acid (Rp-isomer) and its salts; guanosine-2',5'-cyclic monophosphoric acid and its salts; guanosine-2',5'-cyclic monophosphorothioic acid (Sp-isomer) and its salts; and guanosine-2',5'-cyclic monophosphorothioic acid (Rp-isomer) and its salts.

The base that forms a salt with the cyclic nucleoside monophosphate derivative is not particularly limited as long as it is biochemically acceptable and forms a salt with the derivative. Preferred are, for example, alkali metal atoms such as sodium or potassium, and organic bases such as tris-hydroxyaminomethane, among others.

Of these activity enhancers, adenosine-3',5'-cyclic monophosphoric acid or adenosine-3',5'-cyclic monophosphate sodium salt is particularly preferred. These activity enhancers may be used alone, or two or more of these may be used in combination.

The activity enhancer may be incorporated into the cell-free protein synthesis solution of the present invention in advance. If the activity enhancer is unstable in the solution, it is preferably added during the protein synthesis reaction performed in the presence of both the cell-free protein synthesis solution and rubber particles.

The amount of the activity enhancer added is not particularly limited as long as the activity enhancer is at a concentration that can activate (increase) the protein synthesis reaction in the cell-free protein synthesis solution of the present invention. Specifically, the final concentration in the reaction system may usually be at least 0.1 millimoles/liter. The lower limit of the concentration is preferably 0.2 millimoles/liter, more preferably 0.4 millimoles/liter, particularly preferably 0.8 millimoles/liter, while the upper limit of the concentration is preferably 24 millimoles/liter, more preferably 6.4 millimoles/liter, particularly preferably 3.2 millimoles/liter.

The temperature of the cell-free protein synthesis solution of the present invention to which the activity enhancer is added is not particularly limited, but is preferably 0° C. to 30° C., more preferably 10° C. to 26° C.

In addition to the mRNA (translation template) coding for a membrane-associated protein, the cell-free protein synthesis solution of the present invention also contains ATP, GTP, creatine phosphate, creatine kinase, L-amino acids, potassium ions, magnesium ions, and other components required for protein synthesis, and optionally an activity enhancer. Such a cell-free protein synthesis solution can serve as a cell-free protein synthesis reaction system.

Since the germ extract prepared as described in JP-A 2005-218357 contains tRNA in an amount necessary for protein synthesis reaction, addition of separately prepared tRNA is not required when the germ extract prepared as above is used in the cell-free protein synthesis solution. In other words, tRNA may be added to the cell-free protein synthesis solution as necessary.

In the present invention, protein synthesis is performed in the presence of both rubber particles and the cell-free protein synthesis solution containing the mRNA coding for a membrane-associated protein. Specifically, this can be accomplished by adding rubber particles to the cell-free protein synthesis solution at a suitable point either before or after protein synthesis, preferably before protein synthesis.

The rubber particles are preferably present in the cell-free protein synthesis solution at a concentration of 5 to 50 g/L. In other words, 5 to 50 g of rubber particles are preferably present in 1 L of the cell-free protein synthesis solution. When the concentration of rubber particles present in the cell-free protein synthesis solution is less than 5 g/L, a rubber layer may not be formed by separation treatment (e.g. ultracentrifugation) for collecting the rubber particles bound to the synthesized membrane-associated protein, and therefore it may be difficult to collect the rubber particles bound to the synthesized membrane-associated protein. Moreover, when the concentration of rubber particles present in the cell-free protein synthesis solution exceeds 50 g/L, the rubber particles may coagulate, so that the synthesized membrane-associated protein may fail to bind well to the rubber particles. The concentration of rubber particles is more preferably 10 to 40 g/L, still more preferably 15 to 35 g/L, particularly preferably 15 to 30 g/L.

In the protein synthesis in the presence of both rubber particles and the cell-free protein synthesis solution, additional rubber particles may be added as appropriate as the reaction progresses. The cell-free protein synthesis solution and rubber particles are preferably present together during the period when the cell-free protein synthesis system is active, such as 3 to 48 hours, preferably 3 to 30 hours, more preferably 3 to 24 hours after the addition of rubber particles to the cell-free protein synthesis solution.

The rubber particles do not have to be subjected to any treatment, e.g. pretreatment before being combined with the cell-free protein synthesis solution. However, membrane-associated proteins may be removed from the rubber particles with a surfactant beforehand to increase the proportion of the membrane-associated protein desired to be bound by the method of the present invention, among the membrane-associated proteins present on the rubber particles. Thus, in another suitable embodiment of the present invention, the rubber particles used in the present invention are washed with a surfactant before being combined with the cell-free protein synthesis solution.

The surfactant is not particularly limited, and examples include nonionic surfactants and amphoteric surfactants. Nonionic surfactants and amphoteric surfactants, among others, are suitable because they have only a little denaturing effect on the proteins on the membrane, and amphoteric surfactants are especially suitable. Thus, in another suitable embodiment of the present invention, the surfactant is an amphoteric surfactant.

These surfactants may be used alone, or two or more of these may be used in combination.

Examples of the nonionic surfactants include polyoxyalkylene ether nonionic surfactants, polyoxyalkylene ester nonionic surfactants, polyhydric alcohol fatty acid ester nonionic surfactants, sugar fatty acid ester nonionic surfactants, alkyl polyglycoside nonionic surfactants, and polyoxyalkylene polyglucoside nonionic surfactants; and polyoxyalkylene alkylamines and alkyl alkanolamides.

Polyoxyalkylene ether nonionic surfactants or polyhydric alcohol fatty acid ester nonionic surfactants are preferred among these.

Examples of the polyoxyalkylene ether nonionic surfactants include polyoxyalkylene alkyl ethers, polyoxyalkylene alkylphenyl ethers, polyoxyalkylene polyol alkyl ethers, and polyoxyalkylene mono-, di- or tristyryl phenyl ethers. Among these, polyoxyalkylene alkylphenyl ethers are suitable. The polyol is preferably a C2-C12 polyhydric alcohol, such as ethylene glycol, propylene glycol, glycerin, sorbitol, glucose, sucrose, pentaerythritol, or sorbitan.

Examples of the polyoxyalkylene ester nonionic surfactants include polyoxyalkylene fatty acid esters and polyoxyalkylene alkyl rosin acid esters.

Examples of the polyhydric alcohol fatty acid ester nonionic surfactants include fatty acid esters of C2-C12 polyhydric alcohols and fatty acid esters of polyoxyalkylene polyhydric alcohols. More specific examples include sorbitol fatty acid esters, sorbitan fatty acid esters, glycerin fatty acid esters, polyglycerin fatty acid esters, and pentaerythritol fatty acid esters, as well as polyalkylene oxide adducts of the foregoing (e.g. polyoxyalkylene sorbitan fatty acid esters, polyoxyalkylene glycerin fatty acid esters). Among these, sorbitan fatty acid esters are suitable.

Examples of the sugar fatty acid ester nonionic surfactants include fatty acid esters of sucrose, glucose, maltose, fructose, and polysaccharides, as well as polyalkylene oxide adducts of the foregoing.

Examples of the alkyl polyglycoside nonionic surfactants include those having, for example, glucose, maltose, fructose, or sucrose as the glycoside, such as alkyl glucosides, alkyl polyglucosides, polyoxyalkylene alkyl glucosides, and polyoxyalkylene alkyl polyglucosides, as well as fatty acid esters of the foregoing. Polyalkylene oxide adducts of any of the foregoing may also be used.

Examples of the alkyl groups in these nonionic surfactants include C4-C30 linear or branched, saturated or unsaturated alkyl groups. The polyoxyalkylene groups may have C2-C4 alkylene groups, and may have about 1 to 50 moles of added ethylene oxide, for example. Examples of the fatty acids include C4-C30 linear or branched, saturated or unsaturated fatty acids.

Of the nonionic surfactants, polyoxyethyleneethylene (10) octylphenyl ether (Triton X-100) or sorbitan monolaurate (Span 20) is particularly preferred for their ability to moderately remove membrane-associated proteins while keeping the membrane of rubber particles stable and, further, having only a little denaturing effect on the proteins.

Examples of the amphoteric surfactants include zwitterionic surfactants such as quaternary ammonium group/sulfonate group ($-SO_3H$) surfactants, water-soluble quaternary ammonium group/phosphate group surfactants, water-insoluble quaternary ammonium group/phosphate group surfactants, and quaternary ammonium group/carboxyl group surfactants. The acid groups in these zwitterionic surfactants may be salts.

In particular, the zwitterionic surfactant preferably has both positive and negative charges in a molecule. The acid dissociation constant (pKa) of the acid group is preferably 5 or less, more preferably 4 or less, still more preferably 3 or less.

Specific examples of the amphoteric surfactants include ammonium sulfobetaines such as 3-[3-(cholamidopropyl)dimethylamino]-2-hydroxy-1-propanesulfonate (CHAPSO), 3-[3-(cholamidopropyl)-dimethylamino]-propanesulfonate (CHAPS), N,N-bis(3-D-gluconamidopropyl)-cholamide, n-octadecyl-N,N'-dimethyl-3-amino-1-propanesulfonate, n-decyl-N,N'-dimethyl-3-amino-1-propanesulfonate, n-dodecyl-N,N'-dimethyl-3-amino-1-propanesulfonate, n-tetradecyl-N,N'-dimethyl-3-amino-1-propanesulfonate (Zwittergent™-3-14), n-hexadecyl-N,N'-dimethyl-3-amino-1-propanesulfonate, and n-octadecyl-N,N'-dimethyl-3-amino-1-propanesulfonate; phosphocholines such as n-octylphosphocholine, n-nonylphosphocholine, n-decylphosphocholine, n-dodecylphosphocholine, n-tetradecylphosphocholine, and n-hexadecylphosphocholine; and phosphatidylcholines such as dilauroyl phosphatidylcholine, dimyristoyl phosphatidylcholine, dipalmitoyl phosphatidylcholine, distearoyl phosphatidylcholine, dioleoyl phosphatidylcholine, and dilinoleoyl phosphatidylcholine. Of these, 3-[(3-cholamidopropyl)dimethylamino]-propanesulfonate (CHAPS) is particularly preferred for its ability to moderately remove membrane-associated proteins while keeping the membrane of rubber particles stable.

The concentration of the surfactant for the treatment is preferably within three times the critical micelle concentration (CMC) of the surfactant used. The membrane stability of the rubber particles may be reduced if they are treated with the surfactant at a concentration exceeding three times the critical micelle concentration. The concentration is more preferably within 2.5 times, still more preferably within 2.0 times the CMC. The lower limit of the concentration is preferably at least 0.05 times, more preferably at least 0.1 times, still more preferably at least 0.3 times the CMC.

Examples of reaction systems or apparatuses that can be used in the protein synthesis according to the present invention include a batch method (Pratt, J. M. et al., Transcription and Translation, Hames, 179-209, B. D. & Higgins, S. J., eds, IRL Press, Oxford (1984)), a continuous cell-free protein synthesis system in which amino acids, energy sources, and other components are supplied continuously to the reaction system (Spirin, A. S. et al., Science, 242, 1162-1164 (1988)), a dialysis method (Kigawa et al., 21st Annual Meeting of the Molecular Biology Society of Japan, WID 6), and an overlay method (instruction manual of PROTEIOS™ wheat germ cell-free protein synthesis core kit, Toyobo Co., Ltd.). Another method may be to supply template RNA, amino acids, energy sources, and other components as necessary to the protein synthesis reaction system, and discharge the synthesis product or decomposition product as required.

Among these, the overlay method has the advantage of easy operation, but unfortunately rubber particles disperse in the reaction solution and thus are difficult to efficiently bind to the synthesized membrane-associated protein. In contrast, in the dialysis method, since the amino acids used as raw materials of the membrane-associated protein to be synthesized can pass through the dialysis membrane but rubber particles cannot pass therethrough, the dispersal of the rubber particles can be prevented, and thus it is possible to efficiently bind the synthesized membrane-associated protein to the rubber particles. For this reason, the dialysis method is preferred.

The dialysis method refers to a method in which protein synthesis is carried out using the reaction solution for the protein synthesis of the present invention as an internal dialysis solution, and an apparatus in which the internal dialysis solution is separated from an external dialysis solution by a dialysis membrane capable of mass transfer. Specifically, for example, a translation template is added to the synthesis reaction solution excluding the translation template, optionally after pre-incubation for an appropriate amount of time, and then the solution is put in an appropriate dialysis container as the internal reaction solution. Examples of the dialysis container include containers with a dialysis membrane attached to the bottom (e.g. Dialysis Cup 12,000 available from Daiichi Kagaku) and dialysis tubes (e.g. 12,000 available from Sanko Junyaku Co., Ltd.). The dialysis membrane used has a molecular weight cutoff of 10,000 daltons or more, preferably about 12,000 daltons.

The external dialysis solution used is a buffer containing amino acids. Dialysis efficiency can be increased by replacing the external dialysis solution with a fresh solution when the reaction speed declines. The reaction temperature and time are selected appropriately according to the protein synthesis system used. For example, in the case of a system using a wheat-derived germ extract, the reaction may be carried out usually at 10° C. to 40° C., preferably 18° C. to 30° C., more preferably 20° C. to 26° C., for 10 minutes to 48 hours, preferably for 10 minutes to 30 hours, more preferably for 10 minutes to 24 hours.

Since the mRNA coding for a membrane-associated protein contained in the cell-free protein synthesis solution of the present invention is easily broken down, the mRNA may be additionally added as appropriate during the protein synthesis reaction to make the protein synthesis more efficient. Thus, in another suitable embodiment of the present invention, the mRNA coding for a membrane-associated protein is additionally added during the protein synthesis reaction.

The addition time, the number of additions, the addition amount, and other conditions of the mRNA are not particularly limited, and may be selected appropriately.

In the production method of the present invention, the step of collecting the rubber particles may optionally be performed after the step of performing protein synthesis in the presence of both rubber particles and a cell-free protein synthesis solution containing an mRNA coding for a membrane-associated protein to bind the membrane-associated protein to the rubber particles.

The rubber particle collection step may be carried out by any method that can collect the rubber particles. It may be carried out by conventional methods for collecting rubber particles. Specific examples include methods using centrifugation. When the rubber particles are collected by the centrifugation methods, the centrifugal force, centrifugation time, and centrifugation temperature may be selected appropriately so as to be able to collect the rubber particles. For example, the centrifugal force during the centrifugation is preferably 15,000×g or more, more preferably 20,000×g or more, still more preferably 25,000×g or more. Moreover, since increasing the centrifugal force too much is not expected to produce a correspondingly high separation effect, the upper limit of the centrifugal force is preferably 50,000×g or less, more preferably 45,000×g or less. The centrifugation time is preferably at least 20 minutes, more preferably at least 30 minutes, still more preferably at least 40 minutes. Moreover, since increasing the centrifugation time too much is not expected to produce a correspondingly high separation effect, the upper limit of the centrifugation time is preferably 120 minutes or less, more preferably 90 minutes or less.

From the standpoint of maintaining the activity of the membrane-associated protein bound to the rubber particles, the centrifugation temperature is preferably 0° C. to 10° C., more preferably 2° C. to 8° C., particularly preferably 4° C.

The rubber particles and the cell-free protein synthesis solution are separated into the upper and lower layers, respectively, by the centrifugation. The cell-free protein synthesis solution as the lower layer may then be removed to collect the rubber particles bound to the membrane-associated protein. The collected rubber particles may be re-suspended in an appropriate buffer with a neutral pH for storage.

As described above, according to the present invention, a membrane-associated protein can be bound to rubber particles by performing protein synthesis in the presence of both the rubber particles and a cell-free protein synthesis solution containing an mRNA coding for the membrane-associated protein. Thus, another aspect of the present invention relates to a method for binding a membrane-associated protein to rubber particles, which includes the step of performing protein synthesis in the presence of both rubber particles and a cell-free protein synthesis solution containing an mRNA coding for a membrane-associated protein to bind the membrane-associated protein to the rubber particles.

The step of performing protein synthesis in the presence of both rubber particles and a cell-free protein synthesis solution containing an mRNA coding for a membrane-associated protein to bind the membrane-associated protein to the rubber particles is as described above.

(Method for Producing Rubber Product)

The method for producing a rubber product of the present invention includes the steps of: synthesizing rubber from rubber particles produced by the method for producing rubber particles; kneading the rubber with an additive to obtain a kneaded mixture; forming a raw rubber product from the kneaded mixture; and vulcanizing the raw rubber product.

The rubber product is not particularly limited as long as it is a rubber product that can be produced from rubber, preferably natural rubber, and examples include pneumatic tires, rubber rollers, rubber fenders, gloves, and medical rubber tubes.

When the rubber product is a pneumatic tire or, in other words, when the method for producing a rubber product of the present invention is the method for producing a pneumatic tire of the present invention, the raw rubber product forming step corresponds to the step of building a green tire from the kneaded mixture, and the vulcanization step corresponds to the step of vulcanizing the green tire. Thus, the method for producing a pneumatic tire of the present invention includes the steps of: synthesizing rubber from rubber particles produced by the method for producing rubber particles; kneading the rubber with an additive to obtain a kneaded mixture; building a green tire from the kneaded mixture; and vulcanizing the green tire.

<Synthesis Step>

In the synthesis step, rubber is synthesized from the rubber particles produced by the method for producing rubber particles. The synthesis of rubber from the rubber particles may be carried out by conventional methods, such as by mixing the rubber particles with substrates as raw materials of rubber in, for example, a reaction vessel (e.g. a test tube or industrial plant).

<Kneading Step>

In the kneading step, the rubber obtained in the synthesis step is kneaded with an additive to obtain a kneaded mixture.

The rubber obtained in the synthesis step can be produced by subjecting the synthesized rubber particles to the following solidification step.

<Solidification Step>

The synthesized rubber particles are subjected to a solidification step. The method for solidification is not particularly limited, and examples include a method of adding the rubber particles to a solvent that does not dissolve the polyisoprenoid (natural rubber), such as ethanol, methanol, or acetone; and a method of adding an acid to the rubber particles. Rubber (natural rubber) can be recovered as solids from the rubber particles by the solidification step. The obtained rubber (natural rubber) may be dried as necessary before use.

The additive is not particularly limited, and additives used in production of rubber products may be used. For example, in the case where the rubber product is a pneumatic tire, examples of the additive include rubber components other than the rubber obtained from the rubber particles, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

The kneading in the kneading step may be carried out using an open roll mill, a Banbury mixer, an internal mixer, or other rubber kneading machines.

<Raw Rubber Product Forming Step (Green Tire Building Step in the Case of Tire)>

In the raw rubber product forming step, a raw rubber product (green tire in the case of tire) is formed from the kneaded mixture obtained in the kneading step.

The method for forming a raw rubber product is not particularly limited, and methods used to form raw rubber products may be used appropriately. For example, in the case where the rubber product is a pneumatic tire, the kneaded mixture obtained in the kneading step may be extruded according to the shape of a tire component and then formed in a usual manner on a tire building machine and assembled with other tire components to build a green tire (unvulcanized tire).

<Vulcanization Step>

In the vulcanization step, the raw rubber product obtained in the raw rubber product forming step is vulcanized to obtain a rubber product.

The method for vulcanizing the raw rubber product is not particularly limited, and methods used to vulcanize raw rubber products may be used appropriately. For example, in the case where the rubber product is a pneumatic tire, the green tire (unvulcanized tire) obtained in the raw rubber product forming step may be vulcanized by heating and pressing in a vulcanizer to obtain a pneumatic tire.

EXAMPLES

The present invention is specifically explained with reference to examples, but the present invention is not limited to these examples.

Example 1

[Extraction of Total RNA from *Hevea latex*]

Total RNA was extracted from the latex of *Hevea brasiliensis* by the hot phenol method. To 6 mL of the latex were added 6 mL of 100 mM sodium acetate buffer and 1 mL of a 10% SDS solution, and then 12 mL of water-saturated phenol pre-heated at 65° C. The mixture was incubated for five minutes at 65° C., agitated in a vortex mixer, and centrifuged at 7,000 rpm for 10 minutes at room temperature. After the centrifugation, the supernatant was transferred to a new tube, 12 mL of a phenol:chloroform (1:1) solution was added, and the mixture was agitated by shaking for two minutes. After the agitation, the resulting mixture was centrifuged again at 7,000 rpm for 10 minutes at room temperature, the supernatant was transferred to a new tube, 12 mL of a chloroform: isoamyl alcohol (24:1) solution was added, and the mixture was agitated by shaking for two minutes. After the agitation, the resulting mixture was centrifuged again at 7,000 rpm for 10 minutes at room temperature, the supernatant was transferred to a new tube, 1.2 mL of a 3M sodium acetate solution and 13 mL of isopropanol were added, and the mixture was agitated in a vortex mixer. The resulting mixture was incubated for 30 minutes at −20° C. to precipitate total RNA. The incubated mixture was centrifuged at 15,000 rpm for 10 minutes at 4° C., and the supernatant was removed to collect a precipitate of total RNA. The collected total RNA was washed twice with 70% ethanol, and dissolved in RNase-free water.

[Synthesis of cDNA from Total RNA]

cDNA was synthesized from the collected total RNA. The cDNA synthesis was carried out using a PrimeScript II 1st strand cDNA synthesis kit (Takara Bio Inc.) in accordance with the manual.

[Acquisition of CPT Gene from cDNA]

The prepared 1st strand cDNA was used as a template to obtain a CPT gene. PCR was carried out using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The CPT gene was obtained using the following primers.

```
Primer 1:
5'-tttggatccgatggaattatacaacggtgagagg-3'

Primer 2:
5'-tttgcggccgcttattttaagtattccttatgtttctcc-3'
```

A CPT gene (HRT1) was produced as described above. The gene was sequenced to identify the full-length nucleotide sequence and amino acid sequence. The nucleotide sequence of HRT1 is given by SEQ ID NO:3. The amino acid sequence of HRT1 is given by SEQ ID NO:4.

[Vector Construction]

The obtained DNA fragment was subjected to dA addition and then inserted into a pGEM-T Easy vector using a pGEM-T Easy Vector System (Promega) to prepare pGEM-HRT1.

[Transformation of *Escherichia coli*]

*Escherichia coli* DH5a was transformed with the prepared vector, the transformant was cultured on LB agar medium containing ampicillin and X-gal, and *Escherichia coli* cells carrying the introduced target gene were selected by blue/white screening.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection.

It was confirmed by sequence analysis that there were no mutations in the nucleotide sequence of the collected gene inserted into the plasmid.

[Preparation of Vector for Cell-Free Protein Synthesis]

The pGEM-HRT1 obtained in the above [Vector construction] was treated with the restriction enzymes Bam HI and Not I, and inserted into a pEU-E01-His-TEV-MCS-N2 cell-free expression vector that had been treated similarly with the restriction enzymes Bam HI and Not I to prepare pEU-His-N2-HRT1.

[Transformation of *Escherichia coli*]

*Escherichia coli* DH5a was transformed with the prepared vector, the transformant was cultured on LB agar medium containing ampicillin and X-gal, and *Escherichia coli* cells carrying the introduced target gene were selected by colony PCR.

[Plasmid Extraction]

The *Escherichia coli* cells transformed with the plasmid containing the target gene were cultured overnight at 37° C. on LB liquid medium. After the culture, the cells were collected, and the plasmid was collected. A FastGene Plasmid mini kit (Nippon Genetics Co., Ltd.) was used for plasmid collection.

[Preparation of Rubber Particles]

Rubber particles were prepared from *Hevea* latex by five stages of centrifugation. To 900 mL of *Hevea* latex was added 100 mL of 1 M Tris buffer (pH 7.5) containing 20 mM dithiothreitol (DTT) to prepare a latex solution. The latex solution was centrifuged in stages at the following different speeds: 1,000×g, 2,000×g, 8,000×g, 20,000×g, and 50,000×g. Each stage of centrifugation was carried out for 45 minutes at 4° C. To the rubber particle layer left after the centrifugation at 50,000×g was added 3-[(3-cholamidopropyl)dimethylamino]-propanesulfonate (CHAPS) at a final concentration of 0.1 to 2.0×CMC (0.1 to 2.0 times the critical micelle concentration CMC) to wash the rubber particles. After the washing, the rubber particles were collected by ultracentrifugation (40,000×g, 4° C., 45 minutes), and re-suspended in an equal amount of 100 M Tris buffer (pH 7.5) containing 2 mM dithiothreitol (DTT).

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the pEU-His-N2-HRT1 obtained in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The following amounts of materials were added to a dialysis cup (MWCO 12000, Bio-Teck). A total amount of 60 µL of a reaction solution was prepared according to the protocol of the WEPRO7240H expression kit. To the reaction solution was added 1 to 2 mg of the rubber particles. Separately, 650 µL of SUB-AMIX was added to a No. 2 PP container (Maruemu container).

The dialysis cup was set in the No. 2 PP container, and a protein synthesis reaction was initiated at 26° C. The addition of the mRNA and the replacement of the external dialysis solution (SUB-AMIX) were performed twice after the initiation of the reaction.

The reaction was carried out for 24 hours. FIG. 1 shows a schematic diagram illustrating the dialysis process.

[Collection of Reacted Rubber Particles]

The solution in the dialysis cup was transferred to a new 1.5 µL tube, and the reacted rubber particles were collected by ultracentrifugation (40,000×g, 4° C., 45 minutes) and re-suspended in an equal amount of 100 M Tris buffer (pH 7.5) containing 2 mM dithiothreitol (DTT).

[Verification of Bonding of CPT to Rubber Particles]

Bonding of CPT to rubber particles was verified by SDS-PAGE. The protein was stained with CBB.

The SDS-PAGE was carried out using a mini slab gel electrophoresis chamber available from Nihon Eido Corp. The SDS-PAGE separation gel used was 15% acrylamide gel, and common electrophoresis conditions were used. The marker used was XL-ladder (Broad) available from Apro Science Inc.

Moreover, small amounts of the solution in the dialysis cup after the cell-free protein synthesis reaction (before the separation of the protein synthesis solution) and the supernatant obtained by ultracentrifugation for collecting the reacted rubber particles (separated supernatant) were sampled and also subjected to SDS-PAGE.

Figure 2:
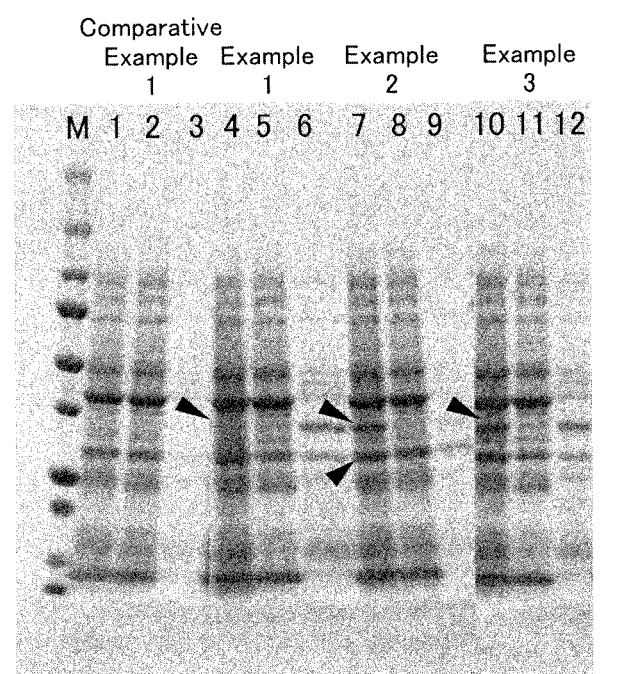
FIG. 2 shows electrophoresis images illustrating the SDS-PAGE results in Examples 1 to 3 and Comparative Example 1.

The SDS-PAGE electrophoresis images in Example 1 (lanes 4 to 6) are shown in FIG. 2. FIG. 2 shows that although the expression of CPT was observed in the cell-free protein synthesis solution immediately after the reaction (before the separation of the protein synthesis solution) as indicated by the arrow, it was not observed in the supernatant obtained after separation for collecting the rubber particles (separated supernatant) and was observed only in the reacted rubber particle part. This proved that the expressed CPT was bound to rubber particles.

Example 2

[Extraction of Total RNA from *Hevea* Latex]

The same procedure as in Example 1 was followed.

[Synthesis of cDNA from Total RNA]

The same procedure as in Example 1 was followed.

[Acquisition of NgBR Gene from cDNA]

The prepared 1st strand cDNA was used as a template to obtain a NgBR gene. PCR was performed using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The NgBR gene was obtained using the following primers.

```
Primer 3:
5'-tttctcgagatggatttgaaacctggagctg-3'
```

Primer 4:
5'-tttctcgagtcatgtaccataattttgctgcac-3'

A NgBR gene (HRTBP) was produced as described above. The gene was sequenced to identify the full-length nucleotide sequence and amino acid sequence. The nucleotide sequence of HRTBP is given by SEQ ID NO: 7. The amino acid sequence of HRTBP is given by SEQ ID NO:8.
[Vector Construction]
The obtained DNA fragment was subjected to dA addition and then inserted into a pGEM-T Easy vector using a pGEM-T Easy Vector System (Promega) to prepare pGEM-HRTBP.
[Transformation of *Escherichia coli*]
The same procedure as in Example 1 was followed but using the prepared vector.
[Plasmid Extraction]
The same procedure as in Example 1 was followed.
[Preparation of Vector for Cell-Free Protein Synthesis]
The pGEM-HRTBP obtained in the above [Vector construction] was treated with the restriction enzyme Xho I, and inserted into a pEU-E01-MCS-TEV-His-C1 cell-free expression vector that had been treated similarly with the restriction enzyme Xho I to prepare pEU-C1-HRTBP.
[Transformation of *Escherichia coli*]
The same procedure as in Example 1 was followed but using the prepared vector.
[Plasmid Extraction]
The same procedure as in Example 1 was followed.
[Preparation of Rubber Particles]
The same procedure as in Example 1 was followed.
[Cell-Free Protein Synthesis Reaction (Step 1: mRNA Transcription Reaction)]
Cell-free protein synthesis was performed using a WEPRO7240H expression kit (CellFree Sciences Co., Ltd.). mRNA transcription reactions were performed using the pEU-C1-HRTBP obtained in the above [Preparation of vector for cell-free protein synthesis] and the pEU-His-N2-HRT1 obtained in [Preparation of vector for cell-free protein synthesis] in Example 1 as templates in accordance with the protocol of the WEPRO7240H expression kit.
[Purification of mRNAs]
After the transcription reactions, the resulting mRNAs were purified by ethanol precipitation.
[Cell-Free Protein Synthesis Reaction (Step 2: Protein Synthesis by Dialysis)]
The same procedure as in Example 1 was followed but using the above mRNAs.
[Collection of Reacted Rubber Particles]
The reacted rubber particles were collected as in Example 1, and re-suspended in an equal amount of 100 M Tris buffer (pH 7.5) containing 2 mM dithiothreitol (DTT).
[Verification of Bonding of CPT and NgBR to Rubber Particles]
Bonding of CPT and NgBR to rubber particles was verified by SDS-PAGE as in Example 1.
Moreover, small amounts of the solution in the dialysis cup after the cell-free protein synthesis reaction (before the separation of the protein synthesis solution) and the supernatant obtained by ultracentrifugation for collecting the reacted rubber particles (separated supernatant) were sampled and also subjected to SDS-PAGE.
The SDS-PAGE electrophoresis images in Example 2 (lanes 7 to 9) are shown in FIG. 2. FIG. 2 shows that although the expression of CPT and NgBR was observed in the cell-free protein synthesis solution immediately after the reaction (before the separation of the protein synthesis solution) as indicated by the arrows, it was not observed in the supernatant obtained after separation for collecting the rubber particles (separated supernatant) and was observed only in the reacted rubber particle part. This proved that the expressed CPT and NgBR were bound to rubber particles.

Comparative Example 1

[Preparation of Rubber Particles]
The same procedure as in Example 1 was followed.
[Cell-Free Protein Synthesis Reaction (Step 1: mRNA Transcription Reaction)]
Cell-free protein synthesis was performed using a WEPRO7240H expression kit (CellFree Sciences Co., Ltd.). An mRNA transcription reaction was performed using a pEU-E01-His-TEV-MCS-N2 cell-free expression vector as a template in accordance with the protocol of the WEPRO7240H expression kit.
[Purification of mRNA]
After the transcription reaction, the resulting mRNA was purified by ethanol precipitation.
[Cell-Free Protein Synthesis Reaction (Step 2: Protein Synthesis by Dialysis)]
The same procedure as in Example 1 was followed but using the above mRNA.
[Collection of Reacted Rubber Particles]
The reacted rubber particles were collected as in Example 1, and re-suspended in an equal amount of 100 M Tris buffer (pH 7.5) containing 2 mM dithiothreitol (DTT).
[SDS-PAGE]
The reacted rubber particles were subjected to SDS-PAGE as in Example 1.
Moreover, small amounts of the solution in the dialysis cup after the cell-free protein synthesis reaction (before the separation of the protein synthesis solution) and the supernatant obtained by ultracentrifugation for collecting the reacted rubber particles (separated supernatant) were sampled and also subjected to SDS-PAGE.
The SDS-PAGE electrophoresis images in Comparative Example 1 (lanes 1 to 3) are shown in FIG. 2. Since Comparative Example 1 is a control experiment using a vector into which no target gene to be expressed was introduced, the protein bands shown in FIG. 2 were mainly the proteins already present in the reagents for the cell-free protein synthesis reaction. By comparing Comparative Example 1 with Examples 1 to 3, the expression of the target proteins was observed as the newly detected protein bands in Examples 1 to 3.

Example 3

[Extraction of Total RNA from *Arabidopsis*]
Total RNA was extracted from *Arabidopsis thaliana* by the hot phenol method. A seedling frozen with liquid nitrogen was ground in a mortar. Thereto were added 400 μL of water-saturated phenol (80° C.) and 400 μL of a RNA extraction buffer (80° C., 100 mM LiCl, 100 mM Tris-HCl (pH 8.0), 10 mM EDTA, and 1% SDS), followed by vortex for 30 seconds. Thereto was added 400 μL of chloroform/isoamyl alcohol (24:1), followed by vortex for 30 seconds. The mixture was centrifuged at 4° C. and 15,000 rpm for 15 minutes, and the upper phase was collected. The upper phase was mixed with 500 μL of 4M LiCl, and then left at −80° C. for one hour. The mixture was centrifuged at 4° C. and 15,000 rpm for 15 minutes, and the supernatant was removed to obtain a precipitate, which was then dissolved in 400 µL of DEPC-treated water. The solution was mixed with 880 µL of ethanol and 40 µL of 3M NaOAc. The mixture was centrifuged at 4° C. and 15,000 rpm for 15 minutes, and the supernatant was removed to obtain a precipitate, which was then washed with 300 µL of 70% ethanol. The mixture was centrifuged at 4° C. and 15,000 rpm for five minutes, and the supernatant was removed to obtain a precipitate, which was then dissolved in 30 µL of DEPC-treated water. In order to remove any genomic DNA contaminant from the extracted total RNA, DNase treatment was performed using DNase I (Takara Bio Inc.) or DNase I recombinant, RNase-free (Roche). In either case, 50 µL of a reaction solution was prepared under the conditions recommended by the manufacturer, and then incubated at 37° C. for 30 minutes. After the reaction, the solution was mixed with 350 µL of DEPC-treated water and 400 µL of phenol, and centrifuged at room temperature and 15,000 rpm for 15 minutes. The upper phase was collected and mixed with 880 µL of ethanol and 40 µL of 3M NaOAc. The mixture was centrifuged at 4° C. and 15,000 rpm for 15 minutes, and the supernatant was removed to obtain a precipitate, which was then washed with 300 µL of 70% ethanol. The mixture was centrifuged at 4° C. and 15,000 rpm, and the supernatant was removed to obtain a precipitate, which was then dissolved in 50 µL of DEPC-treated water.

[Synthesis of cDNA from Total RNA]

The same procedure as in Example 1 was followed.

[Acquisition of CPT Gene from cDNA]

The prepared 1st strand cDNA was used as a template to obtain a CPT gene. PCR was carried out using a KOD-plus-Neo (Toyobo Co., Ltd.) in accordance with the manual. The PCR reaction involved 35 cycles with each cycle consisting of 10 seconds at 98° C., 30 seconds at 58° C., and one minute at 68° C.

The CPT gene was obtained using the following primers.

```
Primer 5:
5'-ggatccgatgttgtctattctctcttc-3'

Primer 6:
5'-actagttcaaacccgacagccaaatcg-3'
```

A single CPT gene (AtCPT5) was produced as described above. The gene was sequenced to identify the full-length nucleotide sequence and amino acid sequence. The nucleotide sequence of AtCPT5 is given by SEQ ID NO:11. The amino acid sequence of AtCPT5 is given by SEQ ID NO:12.

[Vector Construction]

The obtained DNA fragment was subjected to dA addition and then inserted into a pGEM-T Easy vector using a pGEM-T Easy Vector System (Promega) to prepare pGEM-AtCPT5.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The pGEM-AtCPT5 obtained in the above [Vector construction] was treated with the restriction enzymes Bam HI and Spe I, and inserted into a pEU-E01-His-TEV-MCS-N2 cell-free expression vector that had been treated similarly with the restriction enzymes Bam HI and Spe I to prepare pEU-His-N2-AtCPT5.

[Transformation of *Escherichia coli*]

The same procedure as in Example 1 was followed but using the prepared vector.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the pEU-His-N2-AtCPT5 obtained in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Verification of Bonding of AtCPT5 to Rubber Particles]

Bonding of AtCPT5 to rubber particles was verified by SDS-PAGE as in Example 1.

Moreover, small amounts of the solution in the dialysis cup after the cell-free protein synthesis reaction (before the separation of the protein synthesis solution) and the supernatant obtained by ultracentrifugation for collecting the reacted rubber particles (separated supernatant) were sampled and also subjected to SDS-PAGE.

The SDS-PAGE electrophoresis images in Example 3 (lanes 10 to 12) are shown in FIG. 2. FIG. 2 shows that although the expression of AtCPT5 was observed in the cell-free protein synthesis solution immediately after the reaction (before the separation of the protein synthesis solution) as indicated by the arrow, it was not observed in the supernatant obtained after separation for collecting the rubber particles (separated supernatant) and was observed only in the reacted rubber particle part. This proved that the expressed AtCPT5 was bound to rubber particles.

[Measurement of Rubber Synthesis Activity of Rubber Particles]

The rubber synthesis activity of the reacted rubber particles collected in Example 1 and Comparative Example 1 was also measured as follows.

First, 50 mM Tris-HCl (pH 7.5), 2 mM DTT, 5 mM $MgCl_2$, 15 µM farnesyl diphosphate (FPP), 100 µM 1-14C isopentenyl diphosphate ([1-14C]IPP, specific activity 5 Ci/mol), and 10 µL of the rubber particle solution were mixed to prepare a reaction solution (100 µL in total), which was then reacted for 16 hours at 30° C.

After the reaction, 200 µL of saturated NaCl was added to the solution, and the mixture was extracted with 1 mL of diethyl ether to extract isopentenol and the like. Next, polyprenyl diphosphates were extracted from the aqueous phase with 1 mL of BuOH saturated with saline, and then a very long chain polyisoprenoid (natural rubber) was further extracted from the aqueous phase with 1 mL of toluene/hexane (1:1), followed by determination of radioactivity. The radioactivity of each phase was determined by $^{14}C$ counting using a liquid scintillation counter. A higher radioactivity (dpm) indicates higher natural rubber production and higher rubber synthesis activity.

The reacted rubber particles collected in Example 1 had a rubber synthesis activity of 200% relative to Comparative Example 1 set equal to 100%.

These results show that rubber particles bound to CPT exhibited higher rubber synthesis activity than rubber particles not bound to CPT. This also proved that CPT was bound to rubber particles in Example 1.

Comparative Example 2

[Preparation of Vector for Cell-Free Protein Synthesis]

The plasmid GFP/pEU (WO 01/27260) containing a GFP gene described in JP 2005-218357 A was used as a vector for cell-free protein synthesis.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the GFP/pEU obtained in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Verification of Bonding of GFP (Green Fluorescent Protein) to Rubber Particles]

Bonding of GFP to rubber particles was verified by SDS-PAGE as in Example 1.

Moreover, small amounts of the solution in the dialysis cup after the cell-free protein synthesis reaction (before the separation of the protein synthesis solution) and the supernatant obtained by ultracentrifugation for collecting the reacted rubber particles (separated supernatant) were sampled and also subjected to SDS-PAGE.

Figure 3:
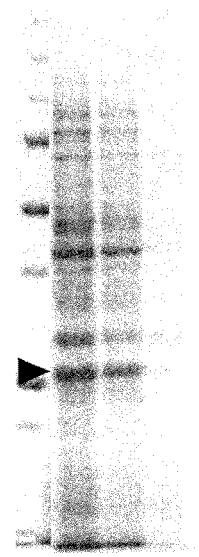
FIG. 3 shows electrophoresis images illustrating the SDS-PAGE results in Comparative Example 2.

The SDS-PAGE electrophoresis images in Comparative Example 2 (lanes 1 to 3) are shown in FIG. 3. FIG. 3 shows that although the expression of GFP was observed in the cell-free protein synthesis solution immediately after the reaction (before the separation of the protein synthesis solution) as indicated by the arrow, it was observed only in the supernatant obtained after separation for collecting the rubber particles (separated supernatant) and was not observed in the reacted rubber particle part. This proved that the expressed non membrane-associated GFP was not bound to rubber particles.

Comparative Example 3

[Preparation of Rubber Particles]

Rubber particles were prepared from *Hevea* latex by five stages of centrifugation. To 900 mL of *Hevea* latex was added 100 mL of 1 M Tris buffer (pH 7.5) containing 20 mM dithiothreitol (DTT) to prepare a latex solution. The latex solution was centrifuged in stages at the following different speeds: 1,000×g, 2,000×g, 8,000×g, 20,000×g, and 50,000×g. Each stage of centrifugation was carried out for 45 minutes at 4° C. To the rubber particle layer left after the centrifugation at 50,000×g was added 3-[(3-cholamidopropyl)dimethylamino]-propanesulfonate (CHAPS) at a final concentration of 1.0 to 2.0×CMC (1.0 to 2.0 times the critical micelle concentration CMC) to wash the rubber particles. After the washing, the rubber particles were collected by ultracentrifugation (40,000×g, 4° C., 45 minutes), and re-suspended in an equal amount of 100 M Tris buffer (pH 7.5) containing 2 mM dithiothreitol (DTT).

[Detachment of Proteins from Rubber Particles]

The rubber particles were treated overnight at 4° C. with CHAPS at a concentration of 10×CMC (10 times the critical micelle concentration CMC) to detach proteins. After the treatment, the washed rubber particles were separated from the aqueous phase containing the detached proteins by ultracentrifugation (40,000×g, 4° C., 45 minutes).

[Re-Binding of Proteins to Rubber Particles by Dialysis Method]

In order to re-bind the proteins to the washed rubber particles, the washed rubber particles and the aqueous phase containing the detached proteins were mixed again, and the mixture was wrapped in a dialysis membrane. The dialysis membrane was submerged in an external solution (100 M Tris buffer (pH 7.5) containing 2 mM dithiothreitol (DTT)) in a volume 1,000 times greater than the internal solution volume to perform dialysis. The dialysis was carried out for a total of eight hours while replacing the external solution with a new one every two hours, thereby removing the surfactant.

[Measurement of Rubber Synthesis Activity of Rubber Particles]

If the proteins are re-bound to the rubber particles by the dialysis process, the rubber synthesis activity of the rubber particles should improve compared to before the dialysis. Accordingly, the rubber synthesis activity of the rubber particles before the dialysis was compared with that after the dialysis. The rubber synthesis activity of the rubber particles was measured as described above.

Then the rubber synthesis activities were expressed in percentage relative to the rubber particles (untreated rubber particles) collected in the above [Preparation of rubber particles], which was set equal to 100%.

Table 1 shows the results.

TABLE 1

|  | Rubber synthesis activity (%) |
| --- | --- |
| Untreated rubber particles | 100 |
| Washed rubber particles (before dialysis) | 5.6 |
| Washed rubber particles (after dialysis) | 4.3 |

As shown in Table 1, the rubber synthesis activity of the rubber particles did not improve from before to after the dialysis. This demonstrated that the proteins cannot be bound to the rubber particles by merely mixing the rubber particles and the proteins.

SEQUENCE LISTING FREE TEXT

SEQ ID NO:1: Primer 1
SEQ ID NO:2: Primer 2
SEQ ID NO:3: Nucleotide sequence of gene coding for HRT1 from *Hevea brasiliensis*
SEQ ID NO: 4: Amino acid sequence of HRT1 from *Hevea brasiliensis*

SEQ ID NO:5: Primer 3
SEQ ID NO:6: Primer 4
SEQ ID NO:7: Nucleotide sequence of gene coding for HRTBP from *Hevea brasiliensis*
SEQ ID NO:8: Amino acid sequence of HRTBP from *Hevea brasiliensis*
SEQ ID NO:9: Primer 5
SEQ ID NO:10: Primer 6
SEQ ID NO: 11: Nucleotide sequence of gene coding for AtCPT5 from *Arabidopsis*
SEQ ID NO:12: Amino acid sequence of AtCPT5 from *Arabidopsis*

The invention claimed is:

1. A method for producing rubber particles bound to a membrane-associated protein, the method comprising the step of performing protein synthesis in a cell-free protein synthesis solution containing an mRNA coding for a membrane-associated protein and rubber particles that bind the membrane-associated protein.

2. The method for producing rubber particles bound to a membrane-associated protein according to claim 1, wherein the cell-free protein synthesis solution contains a germ extract derived from wheat.

3. The method for producing rubber particles bound to a membrane-associated protein according to claim 1, wherein the rubber particles are present in the cell-free protein synthesis solution at a concentration of 5 to 50 g/L.

4. The method for producing rubber particles bound to a membrane-associated protein according to claim 1, wherein the rubber particles are washed with a surfactant before being combined with the cell-free protein synthesis solution.

5. The method for producing rubber particles bound to a membrane-associated protein according to claim 4,
wherein the surfactant is an amphoteric surfactant, and the rubber particles are washed with the surfactant at a concentration within three times a critical micelle concentration of the surfactant.

6. The method for producing rubber particles bound to a membrane-associated protein according to claim 4,
wherein the surfactant is CHAPS.

7. The method for producing rubber particles bound to a membrane-associated protein according to claim 1,
wherein the protein synthesis is carried out by a dialysis method.

8. The method for producing rubber particles bound to a membrane-associated protein according to claim 1,
wherein the mRNA coding for a membrane-associated protein is additionally added during the protein synthesis reaction.

9. A method for producing a pneumatic tire, the method comprising the steps of:
synthesizing rubber from rubber particles produced by the method according to claim 1;
kneading the rubber with an additive to obtain a kneaded mixture;
building a green tire from the kneaded mixture; and
vulcanizing the green tire,
wherein the additive is at least one selected from the group consisting of carbon black, silica, calcium carbonate, alumina, clay, talc, silane coupling agent, zinc oxide, stearic acid, antioxidant, softener, wax, vulcanizing agent, and vulcanization accelerator.

10. A method for producing a rubber product, the method comprising the steps of:
synthesizing rubber from rubber particles produced by the method according to claim 1;
kneading the rubber with an additive to obtain a kneaded mixture;
forming a raw rubber product from the kneaded mixture; and
vulcanizing the raw rubber product.

* * * * *